United States Patent
Balmforth et al.

(10) Patent No.: US 10,144,958 B2
(45) Date of Patent: Dec. 4, 2018

(54) METHYLATION DETECTION METHOD

(71) Applicant: BASE4 INNOVATION LTD, Cambridge, Cambridgeshire (GB)

(72) Inventors: Barnaby Balmforth, Cambridgeshire (GB); Ana Luisa Bras dos Santos Ribeiro da Silva-Weatherley, Cambridgeshire (GB)

(73) Assignee: BASE4 INNOVATION LTD., Cambridge, MA (US)

( * ) Notice: Subject to any disclaimer, the term of this patent is extended or adjusted under 35 U.S.C. 154(b) by 151 days.

(21) Appl. No.: 15/118,628

(22) PCT Filed: Feb. 13, 2015

(86) PCT No.: PCT/GB2015/050422
§ 371 (c)(1),
(2) Date: Aug. 12, 2016

(87) PCT Pub. No.: WO2015/121675
PCT Pub. Date: Aug. 20, 2015

(65) Prior Publication Data
US 2017/0058331 A1   Mar. 2, 2017

(30) Foreign Application Priority Data
Feb. 14, 2014  (GB) .................... 1402644.7

(51) Int. Cl.
*C12Q 1/68* (2018.01)
*C07H 21/00* (2006.01)
*C12Q 1/6827* (2018.01)

(52) U.S. Cl.
CPC ................... *C12Q 1/6827* (2013.01)

(58) Field of Classification Search
CPC ................... C12Q 1/68; C07H 21/00
See application file for complete search history.

(56) References Cited

U.S. PATENT DOCUMENTS

| | | | |
|---|---|---|---|
| 6,331,393 B1 * | 12/2001 | Laird | C12Q 1/6858 435/6.12 |
| 2003/0157510 A1 | 8/2003 | Olek et al. | |
| 2006/0194208 A1 * | 8/2006 | Tetzner | C12Q 1/6886 435/6.12 |
| 2009/0068659 A1 | 3/2009 | Taylor et al. | |
| 2009/0208941 A1 * | 8/2009 | Berlin | C12Q 1/6827 435/6.12 |
| 2010/0173291 A1 * | 7/2010 | Guetta | C12N 5/0603 435/6.12 |
| 2011/0091884 A1 | 4/2011 | Yamakawa | |
| 2013/0017544 A1 | 1/2013 | Eckhardt et al. | |
| 2013/0078626 A1 | 3/2013 | Wasserstrom et al. | |
| 2013/0230887 A1 | 9/2013 | Ong et al. | |
| 2014/0199690 A1 | 7/2014 | Zhao et al. | |

FOREIGN PATENT DOCUMENTS

| | | |
|---|---|---|
| EP | 0 851 033 | 7/1998 |
| EP | 1 882 747 | 7/2007 |
| WO | 00/46398 | 8/2000 |
| WO | 2004/020603 | 3/2004 |
| WO | 2012/112970 | 8/2012 |
| WO | 2013/154898 | 10/2013 |
| WO | 2014/053854 | 4/2014 |
| WO | 2014/167323 | 10/2014 |
| WO | 2014/167324 | 10/2014 |

OTHER PUBLICATIONS

Herman et al.*
International Search Report dated Apr. 23, 2015 in International (PCT) Application No. PCT/GB2015/050422.
Written Opinion of the International Searching Authority dated Apr. 23, 2015 in International (PCT) Application No. PCT/GB2015/050422.
Search Report dated Oct. 27, 2014 in corresponding Great Britain Application No. 1402644.7.
Ferrone et al., "Analysis of genomic methylation level using micellar electrokinetic chromatography with UV detection", Electrophoresis, vol. 34, 2013, pp. 2275-2280.
Le et al. "A sensitive mass spectrometry method for simultaneous qualification of DNA methylation and hydroxymethylation levels in biological samples", Analytical Biochemistry, vol. 412, Jan. 24, 2011, pp. 203-209.
Kaminsky et al., "Methylation SNaPshot: A method for the Quantification of Site-Specific DNA Methylation Levels", Methods in Molecular Biology, vol. 507, 2009, pp. 241-255.

* cited by examiner

*Primary Examiner* — Ethan C Whisenant
(74) *Attorney, Agent, or Firm* — Wenderoth, Lind & Ponack, L.L.P.

(57) ABSTRACT

A method of determining whether a given single nucleotide is methylated or not methylated characterized by the steps of (a) contacting the single nucleotide with one or more hybridization probe types each of which in its unused form; (b) for the relevant probe type causing (i) the single nucleotide to bind to the region resistant to exonucleolytic degradation and the single-stranded region and (ii) the second oligonucleotide to bind to the single nucleotide and the single-stranded nucleotide region; (c) treating the used probe with a methylation-dependent restriction or a methylation-sensitive restriction endonuclease to cleave adjacent the region resistant to exonucleolytic degradation; and thereafter (d) treating the product of step (c) with an exonuclease or a polymerase exhibiting exonuclease activity to liberate either only first or both first and second detectable elements in a detectable state to determine if the single nucleotide is methylated or not.

Figure 1:
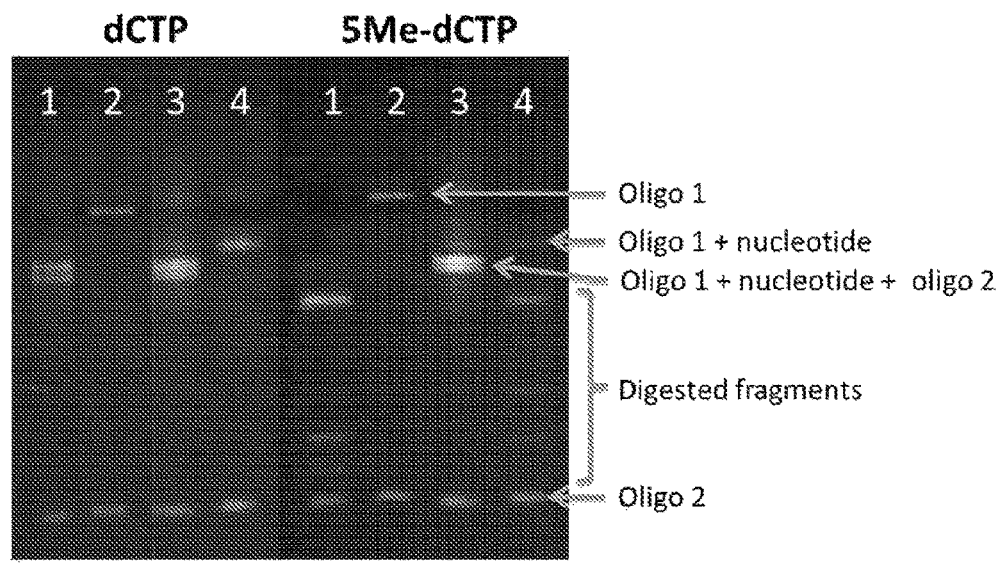

22 Claims, 1 Drawing Sheet
Specification includes a Sequence Listing.

SEQUENCE LISTING

<160> NUMBER OF SEQ ID NOS: 4

<210> SEQ ID NO 1
<211> LENGTH: 113
<212> TYPE: DNA
<213> ORGANISM: Artificial Sequence
<220> FEATURE:
<223> OTHER INFORMATION: single-stranded oligonucleotide precursor
<220> FEATURE:
<221> NAME/KEY: modified_base
<222> LOCATION: (28)..(28)
<223> OTHER INFORMATION: m5c
<220> FEATURE:
<221> NAME/KEY: misc_feature

```
<222> LOCATION: (101)..(102)
<223> OTHER INFORMATION: T bases labelled with Quasar 570
<220> FEATURE:
<221> NAME/KEY: misc_feature
<222> LOCATION: (103)..(103)
<223> OTHER INFORMATION: T base labelled with BHQ-2 quencher
<220> FEATURE:
<221> NAME/KEY: misc_feature
<222> LOCATION: (104)..(105)
<223> OTHER INFORMATION: T bases labelled with Quasar 570
<220> FEATURE:
<221> NAME/KEY: misc_feature
<222> LOCATION: (112)..(113)
<223> OTHER INFORMATION: phosphorothioate linkage

<400> SEQUENCE: 1
gtaggtcctg gaaacgaaaa acggaggcca gaagcaaaaa gcagggacgt gatgttccat      60
gactgatttt ttttcagtc atggaacatc acgtccctgc tttttgcttc tgg             113

<210> SEQ ID NO 2
<211> LENGTH: 20
<212> TYPE: DNA
<213> ORGANISM: Artificial Sequence
<220> FEATURE:
<223> OTHER INFORMATION: single-stranded oligonucleotide precursor
<220> FEATURE:
<221> NAME/KEY: misc_feature
<222> LOCATION: (6)..(7)
<223> OTHER INFORMATION: T bases labelled with Alexa Fluor 633
<220> FEATURE:
<221> NAME/KEY: misc_feature
<222> LOCATION: (8)..(8)
<223> OTHER INFORMATION: T base labelled with BHQ-2 quencher
<220> FEATURE:
<221> NAME/KEY: misc_feature
<222> LOCATION: (9)..(10)
<223> OTHER INFORMATION: T bases labelled with Alexa Fluor 633

<400> SEQUENCE: 2
ctccgttttt cgtttccaga                                                  20

<210> SEQ ID NO 3
<211> LENGTH: 113
<212> TYPE: DNA
<213> ORGANISM: Artificial Sequence
<220> FEATURE:
<223> OTHER INFORMATION: single-stranded oligonucleotide precursor
<220> FEATURE:
<221> NAME/KEY: misc_feature
<222> LOCATION: (101)..(102)
<223> OTHER INFORMATION: T bases labelled with Quasar 570
<220> FEATURE:
<221> NAME/KEY: misc_feature
<222> LOCATION: (103)..(103)
<223> OTHER INFORMATION: T base labelled with BHQ-2 quencher
<220> FEATURE:
<221> NAME/KEY: misc_feature
<222> LOCATION: (104)..(105)
<223> OTHER INFORMATION: T bases labelled with Quasar 570
<220> FEATURE:
<221> NAME/KEY: misc_feature
<222> LOCATION: (112)..(113)
<223> OTHER INFORMATION: phosphorothioate linkage

<400> SEQUENCE: 3
gtaggtcctg gaaacgaaaa acggacgtac gaagcaaaaa gcagggacgt gatgttccat      60
gactgatttt ttttcagtc atggaacatc acgtccctgc tttttgcttc gta             113

<210> SEQ ID NO 4
<211> LENGTH: 20
<212> TYPE: DNA
```

```
<213> ORGANISM: Artificial Sequence
<220> FEATURE:
<223> OTHER INFORMATION: single-stranded oligonucleotide precursor
<220> FEATURE:
<221> NAME/KEY: misc_feature
<222> LOCATION: (6)..(7)
<223> OTHER INFORMATION: T bases labelled with Alexa Fluor 633
<220> FEATURE:
<221> NAME/KEY: misc_feature
<222> LOCATION: (8)..(8)
<223> OTHER INFORMATION: T base labelled with BHQ-2 quencher
<220> FEATURE:
<221> NAME/KEY: misc_feature
<222> LOCATION: (9)..(10)
<223> OTHER INFORMATION: T bases labelled with Alexa Fluor 633

<400> SEQUENCE: 4
gtccgttttt cgtttccaga                                           20
```

METHYLATION DETECTION METHOD

This invention relates to a method for determining whether a given nucleotide derived from a polynucleotide analyte is or is not methylated.

Next generation sequencing of genetic material is already making a significant impact on the biological sciences in general and medicine in particular as the unit cost of sequencing falls in line with the coming to market of faster and faster sequencing machines. Thus, in one such machine, a double-stranded DNA analyte is indirectly sequenced by first being broken down into a plurality of smaller polynucleotide fragments each of which is first adenylated on both ends of one strand so that a single-stranded first oligonucleotide can be bound to both ends of its complement by hybridisation to the unpaired adenine base. The treated fragments so obtained are then size-selected and captured on a surface coated with bound single-stranded second oligonucleotides which themselves are the sequence complement of the first so that in effect a library of surface-bound double-stranded fragments can be created by further hybridisation. In a subsequent clustering step, these library components are then clonally amplified millions of times on the surface using extension and isothermal bridging reactions to utilise unused second oligonucleotides. This, in effect, creates a dense concentration of the polynucleotide fragment bound to the surface through one of its strands. The unbound complementary strand of each fragment is then removed to leave bound single-stranded fragments ready for sequencing. In the sequencing stage, each of these single-stranded fragments is primed and its complementary strand recreated by extension using the polymerase chain reaction and a mixture of the four characteristic nucleotide bases of DNA in dideoxynucleotide triphosphate (ddNTP) form. Each ddNTP type is end-blocked with a moiety which is labelled with a different fluorophore fluorescing at a different wavelength. The extension reaction then takes the form of a cycle of three steps; first the relevant ddNTP is bound to the growing strand; secondly the nucleotide base it contains is identified by illuminating the sample and detecting the wavelength of the fluorescence and finally the end block and its associated fluorophore are removed to allow the next extension event to occur. By this means, the sequence of the complementary strand can be built up base-by-base. It will be appreciated that, whilst this approach can be highly automated and can generate sequence reads of high accuracy, its speed of operation is limited by the rate of the extension cycle. Thus, in practice, use of the technology tends to involve parallel processing of relatively short polynucleotide fragments and assembly of the whole sequence from the various reads obtained therefrom. This in itself can lead to computational complexities and the potential introduction of errors.

More recently, efforts have been made to develop alternative direct sequencing methods. For example, in our previous applications GB1217772.1 (now published as WO2014/053854), GB1306444.9 (now published as WO2014/167323) and GB1306445.6 (now published as WO2014/167324) we have described a new sequencing method which involves progressive pyrophosphorolysis or exonucleolysis of a polynucleotide analyte to generate an ordered stream of single nucleotides which can be captured one-by-one into corresponding droplets in a droplet stream. Thereafter, each droplet can be chemically and/or enzymatically manipulated to reveal the particular single nucleotide it originally contained. In one embodiment, these chemical and/or enzymatic manipulations comprise a method involving the use of one or more two-component oligonucleotide probe types each of which is adapted to be able to selectively capture one of the single nucleotide types from which the analyte is constituted. Typically, in each of such probe types, one of the two oligonucleotide components comprises characteristic fluorophores and in the probe's unused state the ability of these fluorophores to fluoresce remains extinguished by the presence of quenchers located close-by or by self-quenching. In use, when the probe has captured its corresponding single nucleotide, it can be cut by a restriction enzyme rendering it susceptible to subsequent exonucleolysis thereby liberating the fluorophores from the quenchers and/or each other enabling them to fluoresce freely. By this means, the original single nucleotide present in each droplet can be identified indirectly by spectroscopic means.

We have now developed a variant on this method specifically designed to detect the presence or absence of methylation in genetic material and to be applicable to our droplet technology. Understanding whether a given cytosine- or adenine-containing nucleotide in for example a mammalian DNA sample is or is not methylated is an extremely important issue for medicine as the phenomenon is known to be an important regulator in the transcription of genetic material. For example, high levels of methylation relative to the norm have been correlated with a tendency of people to develop malignant tumours. Knowing the degree of methylation in a person's genome may therefore facilitate the early identification and amelioration of such problems. Thus, according to a first aspect of the present invention there is provided a method of determining whether a given single nucleotide is methylated or not methylated characterised by the steps of (a) contacting the single nucleotide with one or more hybridisation probe types each of which in its unused form comprises (1) a first oligonucleotide to which is attached one or more first detectable elements in an essentially undetectable state and which further comprises (i) double- and single-stranded regions and (ii) a region resistant to exonucleolytic degradation attached to the end of the double-stranded region adjacent the single-stranded region and (2) a second single-stranded oligonucleotide to which is attached one or more second detectable elements also in an essentially undetectable state and which is adapted to be at least in part the nucleotide sequence complement of the single-stranded region of the first oligonucleotide; (b) for the relevant probe type causing (i) the single nucleotide to bind to the region resistant to exonucleolytic degradation and the single-stranded region and (ii) the second oligonucleotide to bind to the single nucleotide and the single-stranded nucleotide region to create a substantially double-stranded used probe; either (c1) treating the used probe with a methylation-dependent restriction endonuclease under conditions whereby the used probe is cleaved adjacent the region resistant to exonucleolytic degradation into two double-stranded oligonucleotide products if the single nucleotide is methylated or (c2) treating the used probe with a methylation-sensitive restriction endonuclease under conditions whereby the used probe is cleaved adjacent the region resistant to exonucleolytic degradation into two double-stranded oligonucleotide products if the single nucleotide is not methylated; and thereafter either (d1) treating the product of step (c1) with an exonuclease or a polymerase exhibiting exonuclease activity to liberate either only first or both first and second detectable elements in a detectable state if the single nucleotide is methylated, or only the second detectable elements if not or (d2) treating the product of step (c2) with an exonuclease or a polymerase exhibiting exonuclease activity to liberate either only first or both first and second detectable elements in a detectable state if the single nucleotide is not methylated, or only the second detectable element if the single nucleotide is methylated.

In one embodiment of the invention, the single nucleotide to be determined is generated from a precursor polynucleotide analyte by for example pyrophosphorolysis or exonucleolytic degradation. Such an analyte used here and in other embodiments may suitably comprise a fragment of genetic material; for example a fragment of human or other mammalian DNA or RNA. Suitably, this fragment is many nucleotides long; for example greater than 500, 1,000, 5,000 or even 10,000 nucleotides long. In another embodiment, the pyrophosphorolysis or exonucleolytic degradation is carried out progressively so that a stream of single nucleotides corresponding to the nucleotide sequence of the analyte is generated in a flow system. In yet another embodiment, the single nucleotides in this stream are inserted one-by-one into corresponding empty droplets in a droplet stream so that each droplet contains no more than one single nucleotide. Preferably the ordering of the single nucleotides in the filled droplet stream corresponds to the nucleotide sequence of the analyte and the method of the invention is carried out on individual droplets by inserting the various probe types thereinto before or after the single nucleotide has been introduced or at the same time. Suitably the droplet stream is comprised of a stream of water droplets in oil; preferably water microdroplets in oil as for example disclosed in our earlier applications referred to above.

In step (a) of the method of the invention, the single nucleotide to be determined is contacted with one or more probe types. Each probe type employed is capable of binding to a different single nucleotide type as a consequence of the rule of base-pairing. Thus for DNA there are four different single nucleotide types corresponding to the nucleotide bases guanine (G), cytosine (C), adenine (A) and thymine (T) which pair in a complementary fashion as C-G and A-T and for RNA there are four types corresponding to guanine, cytosine, adenine and uracil (U) where the A and U pair. In one embodiment, one probe type is used in the method corresponding to one of these single nucleotide types; preferably either cytosine or adenine. In another, two probe types are used corresponding to any two pairs of the single nucleotide types mentioned above. In yet another, three types are used corresponding to any triplet of these single nucleotide types. Finally, another embodiment involves the use of all four probe types.

The hybridisation probes employed in the method of the invention are themselves comprised, in their unused state, of two oligonucleotide components. The first oligonucleotide is one which is comprised of double- and single-stranded regions and which has attached thereto one or more first detectable elements in an undetectable state. In one preferred class of first oligonucleotides, these double and single-stranded regions can be derived, or be viewed as being derivable, from a single-stranded precursor oligonucleotide the 3' end of which has been partially folded back and bound in part to itself by complementary nucleotide hybridisation. The product so obtained, sometimes referred to as 'j-shaped' on account of its structural appearance, retains a single-stranded region comprised of the stem of the 'j' beyond the 3' end.

The first oligonucleotide is further characterised by comprising a region resistant to exonucleolytic degradation attached to the end of the double-stranded region adjacent the single-stranded region. In the case of the j-shaped first oligonucleotides referred to above this is located at the 3' end and is achieved by modifying the linkage between the final nucleotides, preferably the final two nucleotides, at this position so that it comprises a resistant moiety such as phosphorothioate instead of the conventional phosphodiester. As such a phosphorothioate linkage exists in two isomeric forms, one embodiment of the invention comprises employing only the more degradation resistant of the two in the first oligonucleotide.

According to a second aspect of the present invention there is therefore provided a hybridisation probe component which in its unused state is resistant to exonucleolytic degradation characterised in that it comprises a j-shaped oligonucleotide having 3' and 5' ends and single- and double-stranded nucleotide regions wherein at least some of the nucleotides adjacent the 3' end are connected by phosphorothioate linkages. In one embodiment the two nucleotides adjacent the 3' end are so connected. In another embodiment, the j-shaped oligonucleotide has attached thereto detectable elements e.g. fluorophores and optionally quenchers to render the fluorophores undetectable.

The second oligonucleotide is one which is single-stranded and also has attached thereto one or more second detectable elements also in an undetectable state. This second oligonucleotide is adapted to be at least in part the nucleotide sequence complement of the single-stranded region of the first oligonucleotide thereby rendering the two capable of hybridising together to form a substantially double-stranded used probe during the process of capturing the single nucleotide. When used with a j-shaped first oligonucleotide, the second oligonucleotide is sometimes referred to as 'i-shaped' and the sequence complementarity between it and the single-stranded region of the first oligonucleotide occurs when the 5' end of the second oligonucleotide is aligned from a point two nucleotides beyond the 3' end of the first oligonucleotide. The net effect of this can be seen as leaving a single un-hybridised nucleotide cavity on the first oligonucleotide, immediately adjacent to the 3' end, which constitutes the site at which the single nucleotide can be captured. It will be appreciated that, as a consequence of nucleotide base-pairing, the nature of this single un-hybridised nucleotide in the cavity will determine the selectivity characteristics of the probe; for example if it comprises a guanine base the probe will be selective for single nucleotides comprising cytosine bases; if it is thymine the probe will be selective for adenine and so on.

In one embodiment, the second oligonucleotide and the single-stranded region on the first oligonucleotide are independently up to 50 nucleotides long, preferably up to 45 nucleotides more preferably in the range 5 to 40 nucleotides and most preferably in the range 10 to 30 nucleotides. In another embodiment, the second oligonucleotide is shorter than the single-stranded region of the first oligonucleotide so that after hybridisation the 5' end of the latter extends beyond the 3' end of the former. The overhang this leads to is typically a few nucleotides in length; e.g. up to 15.

According to a third aspect of the invention there is therefore provided a two-component hybridisation probe which in its unused state is resistant to exonucleolytic degradation characterised in that it comprises a j-shaped first oligonucleotide having 3' and 5' ends and single- and double-stranded nucleotide regions wherein at least some of the nucleotides adjacent the 3' end are connected by phosphorothioate linkages and a second single-stranded oligonucleotide whose nucleotide sequence is at least in part complementary to that of the single-stranded nucleotide region of the first oligonucleotide when aligned from a starting point two nucleotides beyond the 3' end.

As regards the first and second detectable elements which are attached respectively to the first and second oligonucleotide components of the probe, these can in principle be any elements having different characteristic detection properties which can be easily distinguished. Suitably, all of the first detectable elements are of the same one type and all of the second detectable elements are of another type. The first and second detectable elements are attached to the first and second oligonucleotides so as to be in an essentially undetectable state when the probe is in an unused state.

In one embodiment, the detection property is fluorescence and the first and second detectable elements comprise different fluorophore types fluorescing at different characteristic wavelengths. Where this is the case, the first and second fluorophore types are attached to the first and second oligonucleotides so as to be essentially non-fluorescing at those wavelengths where they are designed to be normally detected. For example, although a given fluorophore may exhibit general, low-level background fluorescence across a wide part of the electromagnetic radiation spectrum there will typically be one or a small number of specific wavelengths or wavelength envelopes where the intensity of the fluorescence is at a maximum. It is at one or more of these maxima where the fluorophore is characteristically detected that essentially no fluorescence should occur. In the context of the present invention by the term 'essentially non-fluorescing' or equivalent wording is meant that the intensity of fluorescence of the total number of fluorophores attached to the relevant oligonucleotide at the relevant characteristic wavelength(s) or wavelength envelope is less than 25%; preferably less than 10%; more preferably less than 1% and most preferably less than 0.1% of the corresponding intensity of fluorescence of an equivalent number of free fluorophores.

In principle, any method can be used to ensure that in the probe's unused state the first and second fluorophore types fluoresce less than when free. One approach is to additionally attach quenchers to each of the first and second oligonucleotides in close proximity to their fluorophores. Another is based on the observation that when multiple fluorophores are attached to the same oligonucleotide component in close proximity to each other they tend to self-quench each other sufficiently well that the criterion described in the previous paragraph can be achieved without the need for quenchers. In this context of this patent, what constitutes 'close proximity' between fluorophores or between fluorophores and quenchers will depend on the particular fluorophores and quenchers used and possibly the structural characteristics of the first and second oligonucleotides. Consequently, it is intended that this term be construed with reference to the required outcome rather than any particular structural arrangement on the oligonucleotides. However, and for the purposes of providing exemplification only, it is pointed out that when adjacent fluorophores or adjacent fluorophores and quenchers are separated by a distance corresponding to up to their characteristic Förster distance (typically less than 5 nm) sufficient quenching will generally be achieved.

Preferably each of the first and second oligonucleotides is labelled with up to 20, preferably up to 10 and most preferably up to 5 fluorophores. To obtain maximum advantage, it is preferred that each oligonucleotide is labelled with at least 2 preferably at least 3 fluorophores. Consequently ranges constructed from any permutation of these maxima and minima are specifically envisaged herein. If quenchers are employed, it is likewise preferred that the one or both oligonucleotides are labelled with up to 20, preferably up to 10 and most preferably up to 5 of the same. Whilst it is envisaged that more than one type of fluorophore can be attached to the probe, for example to give it a characteristic fingerprint, it is preferred that all the fluorophores attached to a given probe are of the same type. It will be appreciated however that when multiple hybridisation probes are used in the method the choice of fluorophores on each probe component will need to be carefully chosen so that a signal capable of being both analysed and distinguishing between the ranges of possible outcomes is achieved.

As regards the fluorophores themselves, they can in principle be chosen from any of those conventionally used in the art including but not limited to xanthene moieties e.g. fluorescein, rhodamine and their derivatives such as fluorescein isothiocyanate, rhodamine B and the like; coumarin moieties (e.g. hydroxy-, methyl- and aminocoumarin) and cyanine moieties such as Cy2, Cy3, Cy5 and Cy7. Specific examples include fluorophores derived from the following commonly used dyes: ALEXA dyes, cyanine dyes, ATTO TEC dyes, and rhodamine dyes. Examples also include: ATTO 633 (ATTO-TEC GmbH), TEXAS RED, ATTO 740 (ATTO-TEC GmbH), Rose Bengal, ALEXA FLUOR™ 750 $C_5$-maleimide (Invitrogen), ALEXA FLUOR™ 532 $C_2$-maleimide (Invitrogen) and RHODAMINE RED $C_2$-maleimide and RHODAMINE GREEN as well as phosphoramadite dyes such as QUASAR 570. Alternatively a quantum dot or a near infra-red dye such as those supplied by LI-COR Biosciences can be employed. The fluorophore is typically attached to the oligonucleotide via a nucleotide base using chemical methods known in the art.

Suitable quenchers are those which work by a Förster resonance energy transfer (FRET) mechanism. Non-limiting examples of commercially available quenchers which can be used in association with the above mentioned-fluorophores include but are not limited to DDQ-1, DABCYL, ECLIPSE, IOWA BLACK FQ and RQ, IR Dye-QC1, BHQ-1, -2 and -3 and QSY-7 and -21.

The first and second oligonucleotides employed in the method of the present invention can in principle be manufactured by any of the nucleotide assembly methodologies known in the art including the H-phosphonate method, the phosophodiester synthesis, the phosphotriester synthesis and the phosphite triester synthesis. Preferred are methods employing nucleotide phosphoramadite building blocks on account of their reactivity. In these methods synthesis occurs by sequential addition of the chosen nucleotide phosphoramadite to the growing nucleotide chain at the 5' position in a cyclic four-step process involving de-blocking, coupling, capping and oxidation. The cyclic nature of this process makes it especially amenable to automation and machines to do this are readily available on the market. Where quenchers and/or fluorophores are to be introduced the appropriately labelled nucleotide phosphoramadite is employed at the required point. When the first oligonucleotide is j-shaped it is preferred to use the phosphoramadite method to first make a single-stranded oligonucleotide precursor which is folded by a cycle of rapid heating and slow cooling into a product having the desired structural characteristics.

During step (b) of the method of the invention the single nucleotide to be detected is reacted with the first and second oligonucleotide components of the probe, or the relevant probe if more than one is employed, so that it becomes bound both to the region resistant to exonucleolytic degradation and the second oligonucleotide. By this means a double-stranded used probe is created. In the case of the j-shaped/i-shaped oligonucleotide probe described above, this involves, for example, using a polymerase and a ligase to bind the single nucleotide to the 3' end of the first oligonucleotide and the 5' end of the second oligonucleotide. A wide range of polymerases and ligases can be used to achieve this outcome including but not limited to those derived from readily-available bacterial sources such as bacteriophage T4, *Escherichia Coli* and *Thermus Aquaticus* (Taq). Preferably this step is carried out in an aqueous medium in the presence of excess probe with suitably the molar ratio of single nucleotide to the relevant probe being in the range 1:1 to 1:2000, preferably 1:1 to 1:200, more preferably 1:2 to 1:50 with 1:5 to 1:20 being most preferred. A stoichiometric excess of each of the two enzymes over the target is also suitably employed. In one embodiment, the second oligonucleotide is chosen so it is does not undergo hybridisation with the single-stranded region of the first oligonucleotide until ligation has occurred. It will be appreciated that when more than one probe is used in the method only that probe selective for the single nucleotide in question will undergo step (b) with the others remaining substantially inert and playing no further part in the method.

In step (c) of the method of the present invention the double-stranded used probe created in step (b) is treated with a restriction endonuclease capable of cleaving it at a characteristic recognition site. In one embodiment, hereinafter referred to as step (c1), the used probe is treated with a methylation-dependent restriction endonuclease under conditions whereby it is cleaved adjacent or substantially adjacent to the region resistant to exonucleolytic degradation, on the side of the single nucleotide opposite that bearing the second oligonucleotide, into two largely double-stranded oligonucleotide fragments only if the single nucleotide which has been captured is methylated. By this means, the region resistant to exonucleolytic degradation remains attached to that part of the cleaved probe comprising the second oligonucleotide.

Turning to the methylation-dependent endonuclease, this can for example be LpnPI, which cleaves double-stranded oligonucleotides only at the recognition site 5'-C*CDG-3' (D=A or T and C* is 5-methylcytosine or 5-hydroxymethylcytosine). Here, and assuming that the nucleotides on the first and second oligonucleotides around the cavity where the single nucleotide is to be inserted have been correctly chosen, the required recognition site will only be created when the probe is in its used form and the used probe will be cleaved into separate double-stranded fragments only if the single nucleotide inserted is methylated; i.e. in this particular case if it is C*. Otherwise the double-stranded used probe created in step (b) will remain intact.

In another embodiment, hereinafter referred to as step (c2), the used probe is alternatively treated with a methylation-sensitive restriction endonuclease under conditions whereby the used probe is cleaved adjacent the region resistant to exonucleolytic degradation, on the side of the single nucleotide opposite to that bearing the second oligonucleotide, into two double-stranded oligonucleotide fragments only if the single nucleotide which has been captured is not methylated. By this means, the region resistant to exonucleolytic degradation remains attached to that part of the cleaved probe comprising the second oligonucleotide. For example, the methylation-sensitive endonucleases MspI and HpaII cleave double-stranded oligonucleotides only at a recognition site having the sequence 5'-CC*GG-3' and the DnpI and DnpII endonucleases cleave only at a recognition site having the sequence 5'-GA*TC-3' where A* is methylated adenine. In these instances, and likewise assuming that the nucleotides on the first and second oligonucleotides around the cavity where the single nucleotide is to be inserted have been correctly chosen, the required recognition site will only be created when the probe is in its used form and the used probe will therefore be cleaved into separate double-stranded fragments only if the single nucleotide inserted is non-methylated C or A as the case may be. Otherwise the double-stranded used probe created in step (b) will remain intact.

The site on the used probe at which cleavage by the restriction endonuclease occurs is located on the 5' side of the region resistant to exonucleolytic degradation so that this region will end up in the fragment carrying the original second oligonucleotide. In one embodiment, this cleavage will leave a 5' single-strand overhang on both the resulting fragments. Typically step (c) is also carried out in an aqueous medium with an excess of the endonuclease. The endonuclease employed should be one which will not cleave the used probe if there is a nucleotide missing from its recognition site.

The final step of the method is comprised of either of two alternatives (d1) and (d2) corresponding to treating the product of either step (c1) or step (c2) with a polymerase or exonuclease, suitably one having 3'-5' double-stranded exonuclease activity but neither 5'-3' nor single-stranded exonuclease activity, to liberate the various detectable elements from the used probe or used probe fragments in an unquenched and therefore detectable state. For each of steps (d1) and (d2) there are two scenarios. Thus, if the single nucleotide captured in the used probe is methylated and step (c1) has subsequently been applied, the used probe will by now have been cleaved by the methylation-dependent restriction endonuclease into two double-stranded fragments each carrying respectively the first and second detectable elements. Treatment of these fragments according to step (d1) with an exonuclease or a polymerase exhibiting exonuclease activity will then cause exonucleolytic degradation in the 3'-5' direction and the liberation of a cascade of first and second detectable elements in detectable form as consequence of the quenching or self-quenching effect being removed as the individual nucleotides carrying them are released. Thus, if the first and second detectable elements are different fluorophores, the growth of two different fluorescence signals will be observed. In an alternative embodiment, step (c1) may lead to the fragment carrying the second detectable element being unstable with respect to de-hybridisation into its constituent single strands in which case no exonucleolysis of this fragment will occur, no corresponding liberation of the second detectable elements in unquenched form will take place and only a signal characteristic of the first detectable element will be observed. On the other hand, if the single nucleotide captured in the used probes is not methylated, application of step (c1) will have no effect on the used probe so that when step (d1) is subsequently applied exonucleolysis will only lead to digestion of the used probe as far as the region resistant to exonucleolytic degradation so that only the liberation of second detectable elements will be observed.

It will be readily apparent that the same reasoning can be applied in reverse when the product of step (c2) is treated in step (d2) so that all the various outcomes may be summarised in the following table:

|  | Methylated Single Nucleotide Present. | Non-methylated Single Nucleotide Present. |
| --- | --- | --- |
| Step (d1) - methylation-dependent restriction endonuclease used in step (c1). | Either first only or both first and second detectable elements observed. | Second detectable elements only observed. |

| | Methylated Single Nucleotide Present. | Non-methylated Single Nucleotide Present. |
|---|---|---|
| Step (d2) - methylation-sensitive restriction endonuclease used in step (c2). | Second detectable elements only observed. | Either first only or both first and second elements observed. |

Because the two outcomes in either of step (d1) or step (d2) lead to different observables, it will be apparent the method of the present invention in its various forms allows the user to reliably distinguish between methylated and non-methylated nucleotides.

The polymerase or exonuclease can be added to the reaction mixture at any time, for example either before or after step (c1) or step (c2) has taken place. In a preferred embodiment it is introduced at the same time as the polymerase and ligase in step (b). In this latter case it is preferred that the exonuclease is one which is heat activated and that step (d1) or step (d2) includes the additional sub-step of activating it by heating. Any exonuclease or polymerase exhibiting the exonuclease behaviour described above can be employed.

In one embodiment, the method of the present invention is suitable for analysing single nucleotides derived from a polynucleotide analyte by progressive pyrophosphorolysis or exonucleolytic degradation thereof. Typically the single nucleotides analysed are nucleotide triphosphates preferably ones comprising a deoxyribose moiety (dNTP). Where an exonuclease is used to generate the single nucleotide the initially formed nucleotide mono- and diphosphates may be converted into their corresponding triphosphates using for example a kinase.

In another embodiment, the method of the present invention is used in combination with the droplet sequencing technology described in those of our patent applications identified above; the contents of which are incorporated herein by reference. In one preferred example of this sequencing technology, a stream of droplets, at least some of which contain a single nucleotide triphosphate, are generated from the precursor analyte by progressive pyrophosphorolysis. In another embodiment, the ordering of the nucleotide triphosphates in the stream of droplets corresponds to the sequence of nucleotides in the analyte. In a further embodiment, the method of the present invention is applied to each droplet in turn by inserting thereinto the required hybridisation probes, restriction endonucleases, ligase and exonuclease or polymerase exhibiting exonuclease activity at an appropriate point in the droplet stream. In the case where the detectable elements are fluorophores, each droplet may then subsequently be inspected to determine the nature of the fluorescence being emitted. This can be done, for example, by using a photodetector which, in turn, is capable of generating an electrical signal which can be further processed and analysed by a microprocessor and associated computer algorithms.

The method of the present invention will now be illustrated by the following Examples and Figures.

EXAMPLE 1

A 113 nucleotide single-stranded oligonucleotide precursor (ex. ATDBIO) having the nucleotide base sequence:

(SEQ ID NO: 1)
(5') GTAGGTCCTGGAAACGAAAAACGGAGGmCCAGAAGCAAAAAGCAGG

GACGTGATGTTCCATGACTGATTTTTTTTCAGTCATGGAACATCACGTC

CCTGCXXQXXGCTTCTG-G(3')

wherein X are T bases labelled with QUASAR 570 (fluorophore), Q are T bases labelled with BHQ-2 quencher, mC are 5-methylcytosine nucleotides and '-' is a phosphorothioate linkage, is folded about the 70$^{th}$ nucleotide base by heating an aqueous solution of it to 95° C. and then cooling slowly back to room temperature at a rate of 10 minutes per ° C. At the end of this time, a closed-loop ended probe according to the present invention is formed in which the 67$^{th}$ to 74$^{th}$ nucleotide bases (all here T) comprise a single-stranded nucleotide loop region.

A second, 20-nucleotide, single-stranded oligonucleotide precursor (ex. ATDBIO) having the nucleotide base sequence:

(SEQ ID NO: 2)
(5') CTCCGYYQYYCGTTTCCAGA(3')

wherein Y are T bases labelled with ALEXA FLUOR 633 (fluorophore) and Q are T bases labelled with BHQ-2 quencher, is mixed in solution with an equimolar concentration of the first oligonucleotide precursor and with HAEMOKLENTAQ DNA polymerase, Taq DNA ligase, AXOL restriction endonuclease and KOD EXTREME HOT START DNA polymerase. A solution containing either methylated or non-methylated dCTP (deoxycytidine triphosphate) is then added.

The prepared mix is incubated at 50° C. for one hour, allowing the following enzymatic steps to take place:
1. The HAEMOKLENTAQ polymerase incorporates the dCTP nucleotides onto the 3'-recessed ends of the first oligonucleotides.
2. The Taq ligase ligates the second oligonucleotides onto the 3'-recessed ends of only those first oligonucleotides which have had a dCTP incorporated, creating 'completed' capture molecules.
3. In the case that the incorporated dCTPs were methylated, the AXOL restriction endonuclease cleaves each completed capture molecule into two pieces. In the case that the incorporated dCTPs were not methylated, no cleavage occurs.

Following these steps, the temperature is raised to 70° C. to activate the KOD EXTREME HOT START polymerase and is held at this temperature for 15 minutes. In the case that the incorporated dCTPs were not methylated, the completed capture molecules are subjected to 3'-5' digestion by the polymerase, releasing the ALEXA FLUOR 633 fluorophores into solution which are then free to fluoresce. In the case that the incorporated dCTPs were methylated, the cleaved half of the completed capture molecules containing the second oligonucleotide will melt and so will not be susceptible to degradation by the polymerase. In this case the other cleaved half of the completed capture molecule will be susceptible to degradation, releasing QUASAR 570 fluorophores into solution which are then free to fluoresce. By detection of the characteristic fluorescence spectrum of the resulting solution it is thus possible to infer whether the dCTP nucleotides added to the original mixture were methylated or non-methylated in nature.

The result of steps 1-3 are shown in FIG. 1 for both methylated and non-methylated dCTP. In this gel electrophoresis image the lanes marked '1' show the result of the full reaction of steps 1-3, lanes marked '2' show the reaction in the absence of any nucleotides, lanes marked '3' in the absence of AXOL restriction endonuclease and lanes marked '4' in the absence of ligase. It can clearly be seen that the full reaction in the presence of non-methylated dCTP (leftmost lane '1') results in a pair of bands (due to different possible structural arrangements) corresponding to the combination of the two oligonucleotide precursors and dCTP into a single construct. There is no difference observed between the reaction in the presence and absence of AXOL (lanes 1 & 3), indicating that the restriction endonuclease has zero activity in this case. For the reaction in the presence of methylated dCTP (rightmost four lanes), the same outcome is observed in the absence of AXOL (lane 3), but in the presence of AXOL (lane 1) the resulting DNA fragment is efficiently cleaved by the restriction endonuclease, resulting in a number of bands corresponding to the resulting DNA fragments.

Figure 2:
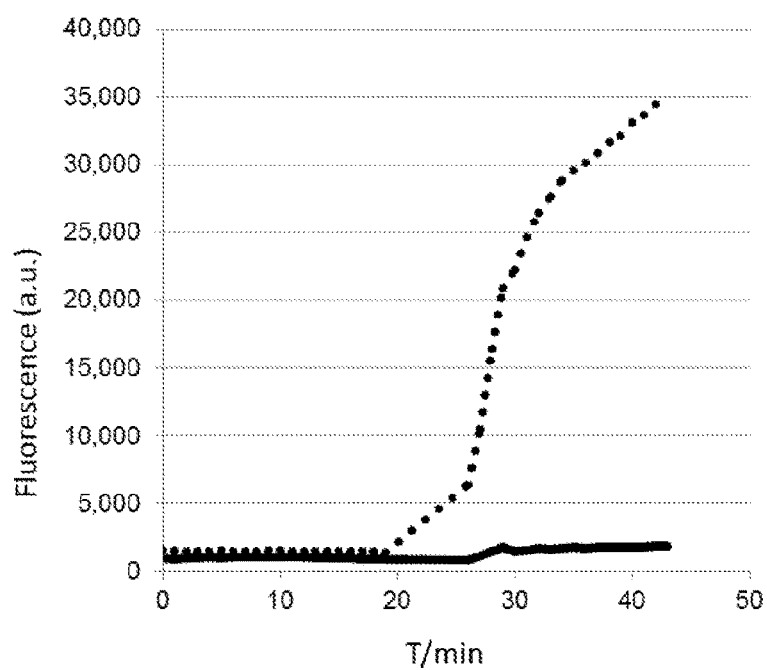

FIG. 2 shows the result of the exonucleolytic digestion by a polymerase of the products obtained from steps 1-3 in the presence (broken line) and absence (solid line) of dCTP. The polymerase is activated by temperature increase at time T=20 minutes and a substantial increase in fluorescence is observed when the dCTP is present while very little change is observed when the dCTP is absent.

EXAMPLE 2

A 113 nucleotide single-stranded oligonucleotide precursor (ex. ATDBIO) having the nucleotide base sequence:

(SEQ ID NO: 3)
(5')GTAGGTCCTGGAAACGAAAAACGGACGTACGAAGCAAAAAGCAGGG

ACGTGATGTTCCATGACTGATTTTTTTTTCAGTCATGGAACATCACGTCC

CTGCXXQXXGCTTCGT-A(3')

wherein X are T bases labelled with QUASAR 570 (fluorophore), Q are T bases labelled with BHQ-2 quencher, mC are 5-methylcytosine nucleotides and '-' is a phosphorothioate linkage, is folded about the $70^{th}$ nucleotide base by heating an aqueous solution of it to 95° C. and then cooling slowly back to room temperature at a rate of 10 minutes per ° C. At the end of this time, a closed-loop ended probe according to the present invention is formed in which the $67^{th}$ to $74^{th}$ nucleotide bases (all here T) comprise a single-stranded nucleotide loop region.

A second, 20-nucleotide, single-stranded oligonucleotide precursor (ex. ATDBIO) having the nucleotide base sequence:

(SEQ ID NO: 4)
(5')GTCCGYYQYYCGTTTCCAGA(3')

wherein Y are T bases labelled with ALEXA FLUOR 633 (fluorophore) and Q are T bases labelled with BHQ-2 quencher, is mixed in solution with equimolar concentration of the first oligonucleotide precursor and with HAEMOKLENTAQ DNA polymerase, Taq DNA ligase, BSIWI restriction endonuclease and KOD EXTREME HOT STARTDNA polymerase. A solution containing either methylated or non-methylated dCTP is then added.

The prepared mix is incubated at 50° C. for one hour, allowing the following enzymatic steps to take place:
 1. The HAEMOKLENTAQ polymerase incorporates the dCTP nucleotides onto the 3'-recessed ends of the first oligonucleotides.
 2. The Taq ligase ligates the second oligonucleotides onto the 3'-recessed ends of only those first oligonucleotides which have had a dCTP incorporated, creating 'completed' capture molecules.
 3. In the case that the incorporated dCTPs were not methylated, the AXOL restriction endonuclease cleaves each completed capture molecule into two pieces. In the case that the incorporated dCTPs were methylated, no cleavage occurs.

Following these steps, the temperature is raised to 70° C. to activate the KOD EXTREME HOT START polymerase and is held at this temperature for 15 minutes. In the case that the incorporated dCTPs were methylated, the completed capture molecules are subjected to 3'-5' digestion by the polymerase, releasing the ALEXA FLUOR 633 fluorophores into solution which are then free to fluoresce. In the case that the incorporated dCTPs were not methylated, the cleaved half of the completed capture molecules containing the second oligonucleotide will melt and so will not be susceptible to degradation by the polymerase. In this case the other cleaved half of the completed capture molecule will be susceptible to degradation, releasing QUASAR 570 fluorophores into solution which are then free to fluoresce. By detection of the characteristic fluorescence spectrum of the resulting solution it is thus possible to infer whether the dCTP nucleotides added to the original mixture were methylated or non-methylated in nature.

The invention claimed is:

1. A method of determining whether a given single nucleotide is methylated or not methylated, the method comprising: (a) contacting the single nucleotide with one or more hybridisation probe types each of which in its unused form comprises (1) a first oligonucleotide to which is attached one or more first detectable elements in an essentially undetectable state and which further comprises (i) double- and single-stranded regions and (ii) a region resistant to exonucleolytic degradation attached to the end of the double-stranded region adjacent the single-stranded region and (2) a second single-stranded oligonucleotide to which is attached one or more second detectable elements also in an essentially undetectable state and which is adapted to be at least in part the nucleotide sequence complement of the single-stranded region of the first oligonucleotide; (b) causing (i) the single nucleotide to bind to the region resistant to exonucleolytic degradation and the single-stranded region and (ii) the second oligonucleotide to bind to the single nucleotide and the single-stranded nucleotide region to create a substantially double-stranded used probe; either (c1) treating the used probe with a methylation-dependent restriction endonuclease under conditions whereby the used probe is cleaved adjacent the region resistant to exonucleolytic degradation into two double-stranded oligonucleotide products if the single nucleotide is methylated or (c2) treating the used probe with a methylation-sensitive restriction endonuclease under conditions whereby the used probe is cleaved adjacent the region resistant to exonucleolytic degradation into two double-stranded oligonucleotide products if the single nucleotide is not methylated; and thereafter either (d1) treating the product of step (c1) with an exonuclease or a polymerase exhibiting exonuclease activity to liberate either only first or both first and second detectable elements in a detectable state if the single nucleotide is methylated, or only the second detectable elements if the single nucleotide is not methylated or (d2) treating the product of step (c2) with an exonuclease or a polymerase exhibiting exonuclease activity to liberate either only first or both first and second detectable elements in a detectable state if the single nucleotide is not methylated, or only the second detectable element if the single nucleotide is methylated.

2. The method of claim 1, wherein the first oligonucleotide is j-shaped and the second oligonucleotide is i-shaped.

3. The method of claim 1, wherein the end of the first oligonucleotide adjacent the site at which the single nucleotide is bound is the 3' end.

4. The method of claim 1, wherein the region resistant to exonucleolytic degradation includes a phosphorothioate linkage between two nucleotides.

5. The method of claim 1, wherein the second oligonucleotide is at least partly the nucleotide sequence complement of the single-stranded region of the first oligonucleotide starting from a point located two nucleotides beyond the end of the double-stranded region.

6. The method of claim 1, wherein the double-stranded used probe has a single-stranded overhang region.

7. The method of claim 1, wherein two or more probes are employed and wherein in each case the nucleotide on the single-stranded region immediately adjacent the region resistant to exonucleolytic degradation is selective for a different single nucleotide comprised of a different nucleotide base.

8. The method of claim 1, wherein two different probes comprised of two different first oligonucleotides are employed and in that the two different nucleotides on the single-stranded region adjacent the region resistant to exonucleolytic degradation are comprised of one of the pairs of nucleotide bases guanine and cytosine; adenine and thymine; or adenine and uracil.

9. The method of claim 1, wherein four different probes comprised of four different first oligonucleotides are employed and in that the four different nucleotides on the single-stranded region adjacent the region resistant to exonucleolytic degradation are comprised of either (a) one of the four nucleotide bases guanine, cytosine, adenine and thymine or (b) one of the four nucleotide bases guanine, cytosine, adenine and uracil.

10. The method of claim 7, wherein each first oligonucleotide is comprised of its own characteristic detectable elements.

11. The method of claim 1, wherein at least some of the first oligonucleotide types used comprise a plurality of first detectable elements.

12. The method of claim 1, wherein each second oligonucleotide comprises a plurality of second detectable elements.

13. The method of claim 1, wherein the first and second detectable elements further comprise different fluorophores or quantum dots each exhibiting different detection characteristics.

14. The method of claim 1, wherein the detectable elements are fluorophores which are rendered undetectable in the probe by the presence of quenchers or by mutual self-quenching.

15. The method of claim 1, wherein the exonuclease possesses 3'-5' double-stranded exonuclease activity but no 5'-3' exonuclease activity and no single-stranded exonuclease activity.

16. The method of claim 1, wherein the exonuclease used in step (d1) or step (d2) is one which is activated by heat.

17. The method of claim 1, wherein the methylation-dependent or methylation-sensitive restriction endonuclease cleaves the used probe so that region resistant to exonucleolytic degradation remains attached to that part of the cleaved probe comprising the second oligonucleotide.

18. The method of claim 1, further comprising the step of (e) detecting the various detectable elements liberated in step (d1) or step (d2).

19. The method of claim 1, wherein the single nucleotide is derived from a polynucleotide analyte by progressive pyrophosphorolysis or exonucleolytic degradation.

20. The method of claim 1, which is carried out in a droplet containing a single nucleotide comprising a nucleotide triphosphate.

21. The method of claim 20, which is applied to a stream of droplets at least some of which contain a single nucleotide triphosphate derived from a polynucleotide analyte.

22. The method of claim 21, wherein the ordering of the single nucleotide triphosphates in the droplets in the droplet stream corresponds to the nucleotide sequence of the analyte.

* * * * *